United States Patent [19]

O'Hanley et al.

[11] Patent Number: 4,736,017

[45] Date of Patent: Apr. 5, 1988

[54] CHEMICALLY DEFINED VACCINE AGAINST URINARY INFECTIONS

[75] Inventors: Peter O'Hanley; Gary K. Schoolnik; David Lark, all of Palo Alto, Calif.; Stanley Falkow, Seattle, Wash.

[73] Assignee: The Board of Trustees of the Leland Stanford Junior University, Stanford, Calif.

[21] Appl. No.: 605,287

[22] Filed: Apr. 30, 1984

[51] Int. Cl.[4] .................... C07K 13/00; C07K 15/04; A61K 39/08

[52] U.S. Cl. .................... 530/350; 530/300; 530/324; 530/806; 530/820; 530/825; 424/88; 424/92; 514/2; 514/12

[58] Field of Search ............ 424/88, 92; 260/112 R, 260/112.5 R; 514/2, 12; 530/350, 300, 324, 806, 820, 825

[56] References Cited

U.S. PATENT DOCUMENTS 4,554,101 11/1985 Hopp ........................ 514/2
4,606,919 8/1986 Stojkovic et al. ............ 424/92

FOREIGN PATENT DOCUMENTS 0048881 4/1982 European Pat. Off. ......... 424/92
WO/8505037 11/1985 PCT Int'l Appl.

OTHER PUBLICATIONS

Wilson et al, "The Structure of an Antigenics Determinant in a Protein" Cell, vol. 37, 1984, pp. 767-768.
Nunberg et al, "Method to Map Antigenic Determinants . . . Protein Gp. 70" PNAS 81, 1984, pp. 3675-3679.
C. A. No. 108631z, vol. 101; Rothhard et al. (J. Exp. Med. 1984 160C.) pp. 208-221.
O'Hanley et al, Mannose-Sensitive and Gal-Gal Binding E. Coli pili . . . Strains, J. Exp. Med. 158, (1983), pp. 1713-1719.
C.A. No. 1068631z, Strain-specific and common epitopesz gondirecal pili, Jonathan et al. vol (101) 1984.
Rothhard et al, Current Communication in Molecular Biology, et Lauer et al, 1985, pp. 161-168.
Synthetic Peptides as Antigen, ed Porter et al., 1986, pp. 184-193 (varies).

Primary Examiner—John Kight
Assistant Examiner—Garnette D. Draper
Attorney, Agent, or Firm—Ciotti & Murashige, Irell & Manella

[57] ABSTRACT

A vaccine effective in protecting mammals against urinary infections is prepared from purified Gal-Gal pilus proteins or fragments thereof.

7 Claims, 2 Drawing Sheets

---

Primary Protein Structure of HU849 Pilin:

```
1                                                              20
Ala Pro Thr Ile Pro Gln Gly Gln Gly Lys Val Thr Phe Asn |Gly Thr Val Val Asp Ala
21                                                             40
Pro Cys Ser Ile Ser Gln Lys Ser Ala Asp Gln Ser Ile Asp Phe Gly Gln Leu Ser Lys
41                                                             60
Ser Phe Leu Glu Ala Gly Gly Val Ser Lys Pro Met Asp Leu Asp Ile Glu Leu Val Asn
61                                                             80
Cys Asp Ile Thr Ala Phe Lys Gly Gly Asn| Gly Ala Lys Lys Gly Thr Val Lys |Leu Ala
81                                                            100
Phe Thr Gly Pro Ile Val Asn Gly His Ser Asp Glu Leu Asp Thr Asn Gly Gly Thr Gly
101                                                           120
Thr Ala Ile Val Val Gln Gly Ala Gly Lys| Asn Val Val Phe Asp Gly Ser Glu Gly Asp
121                                                           140
Ala Asn Thr Leu Lys| Asp Gly Glu Asn Val Leu His |Tyr Thr Ala Val Val Lys Lys Ser
141                                                           160
Ser Ala Val Gly Ala Ala Val Thr Glu Gly Ala Phe Ser Ala Val Ala Asn Phe Asn Leu
161     163
Thr Tyr Gln|
```

FIG. 1

Primary Protein Structure of HU849 Pilin:

```
1                                                                    20
Ala Pro Thr Ile Pro Gln Gly Gln Gly Lys Val Thr Phe Asn|Gly Thr Val Val Asp Ala
21                                                                   40
Pro Cys Ser Ile Ser Gln Lys Ser Ala Asp Gln Ser Ile Asp Phe Gly Gln Leu Ser Lys
41                                                                   60
Ser Phe Leu Glu Ala Gly Gly Val Ser Lys Pro Met Asp Leu Asp Ile Glu Leu Val Asn
61                                                                   80
Cys Asp Ile Thr Ala Phe Lys Gly Gly Asn|Gly Ala Lys Lys Gly Thr Val Lys|Leu Ala
81                                                                   100
Phe Thr Gly Pro Ile Val Asn Gly His Ser Asp Glu Leu Asp Thr Asn Gly Gly Thr Gly
101                                                                  120
Thr Ala Ile Val Val Gln Gly Ala Gly Lys|Asn Val Val Phe Asp Gly Ser Glu Gly Asp
121                                                                  140
Ala Asn Thr Leu Lys|Asp Gly Glu Asn Val Leu His|Tyr Thr Ala Val Val Lys Lys Ser
141                                                                  160
Ser Ala Val Gly Ala Ala Val Thr Glu Gly Ala Phe Ser Ala Val Ala Asn Phe Asn Leu
161     163
Thr Tyr Gln|
```

| Recombinant strain | Receptor specificity | Residue No. | | | | | |
|---|---|---|---|---|---|---|---|
| | | 1 | 2 | 3 | 4 | 5 | 6 |
| HU849 | Gal-Gal | Ala | Pro | Thr | Ile | Pro | Gln |
| SH48 | Mannose | – | Ala | Ala | Thr | Thr | Val |

| | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|
| HU849 | Pro | Gln | Gly | Gln | <u>Gly</u> | Lys | <u>Val</u> | Thr | <u>Phe</u> | Asn | <u>Gly</u> | Thr | <u>Val</u> | <u>Val</u> | Asp |
| SH48 | Thr | Val | Asn | Gly | <u>Gly</u> | Thr | <u>Val</u> | His | <u>Phe</u> | Lys | <u>Gly</u> | Glu | <u>Val</u> | <u>Val</u> | Asn |

| | 20 | 21 | 22 | 23 | 24 | 25 | 26 | 27 | 28 | 29 | 30 | 31 |
|---|---|---|---|---|---|---|---|---|---|---|---|---|
| HU849 | <u>Ala</u> | Pro | <u>Cys</u> | Ser | Ile | Ser | Gln | Lys | Ser | Ala | <u>Asp</u> | <u>Gln</u> |
| SH48 | <u>Ala</u> | Ala | <u>Cys</u> | Ala | Val | Asp | Ala | Gly | (Thr) | Val | <u>Asp</u> | <u>Gln</u> |

| | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|
| HU849 | Ser | Ile | Asp | Phe | <u>Gly</u> | <u>Gln</u> | Leu | Ser | Lys | Ser | Phe | <u>Leu</u> | Glu | Ala | Gly |
| SH48 | Thr | Val | Gln | Leu | <u>Gly</u> | <u>Gln</u> | Val | Arg | Thr | Ala | Thr | <u>Leu</u> | Ala | Gln | Glu |

(conserved positions are underlined)

FIG. 2

CHEMICALLY DEFINED VACCINE AGAINST URINARY INFECTIONS

DESCRIPTION

1. Technical Field

The present invention relates to the field of immunizing humans or animals against infection. More specifically, it relates to vaccination of such subjects with amino acid sequences capable of raising antibodies against organisms infecting the urinary tract. In particular, it relates to use of vaccines which correspond in amino acid sequence to portions of a protein associated with the pili structures of pathogenic organisms.

2. Background Art

Urinary infections constitute a fairly serious medical problem in the United States and the developed world. Approximately 1–5% of the population of the United States is documented to suffer from recurrent urinary tract infection. Approximately 0.1% of these cases encounter the complication of necrotizing pyelitis. Substantially larger numbers of the population, while not afflicted with recurrent infection, are at potential risk to serious complications, even with one episode of pyelonephritis because of an underlying medical condition. Persons at risk include those who have diabetes mellitus (approximately 10 million in the United States), the elderly, persons with renal insufficiency, users of excessive quantities of analgesics, and persons whose immune systems are suppressed e.g., patients being treated with chemotherapy for neoplasms. All of these individuals are at risk for serious complications, permanent disability, and even death from urinary infections.

It would be helpful to provide an effective vaccine which would protect the relevant members of the population from urinary infection. Not only would this prevent the suffering and debilitation now occasioned by the onset of actual infection, it also obviates the need for administration of antibiotics which would be required to treat it. Such avoidance lessens the selective pressure on the infectious biomass caused by excessive use of antibiotics, and delays the appearance of resistant strains.

Because the target infections are not usually regarded as an imminent life-threatening risks, it is necessary to provide a vaccine which itself offers little or no risk. Materials which have been available heretofore as active ingredients of such vaccines are limited to microorganisms having attenuated pathogenicity and to impure protein preparations which are likely to elicit unwanted immunogenic responses and/or result in undesirable side effects. The present invention provides an active vaccine which is a chemically defined, pure protein. It is, therefore, non-infectious. It elicits specific antibodies against the organelles of *E. coli* uropathogens responsible for the colonization of the urinary tract, considered the first step in infection.

DISCLOSURE OF THE INVENTION

It has been found that amino acid sequences which represent fragments of a peptide derived from a specific type of pili, associated with most uropathogenic *E. coli*, have desirable properties in acting as the active ingredient in vaccines against urinary infections in humans. The "Gal-Gal" pili associated with uropathogenic strains of *E. coli* are highly associated with the targeted infections. Other pili subtypes are not. Accordingly, the antigenic domains of the Gal-Gal pilus protein are highly effective and specific in generating antibodies to urinary pathogens, and because of their defined nature and relatively small size, are obtainable in practical quantities and in pure form.

Accordingly, in one aspect, the invention relates to a vaccine effective in preventing uropathogenic infections in humans, which vaccine comprises at least one antigenic determinant of Gal-Gal pilus protein. The invention also relates to the purified amino acid sequences of the subject antigenic determinants and to the purified 163 amino acid sequence of the pilus protein. In another aspect, the invention relates to protecting humans against urinary infections by administration of the vaccines. The invention also relates to methods of producing the active component of the vaccine by isolation of the Gal-Gal pilus protein, and subsequent hydrolysis, followed by purification of the desired sequence.

BRIEF DESCRIPTION OF THE DRAWINGS

FIG. 1 shows the amino acid sequence of the Gal-Gal pilus protein of HU849, and the antigenic determinants.

FIG. 2 shows a comparison of the N-terminal sequences of Gal-Gal binding pilin derived from HU849 and MS pilin from SH48.

MODES OF CARRYING OUT THE INVENTION

A. Definitions

As used herein "corresponding to an antigenic determinant of Gal-Gal pilus protein" refers to an amino acid sequence which is homologous with, or substantially functionally equivalent to the analogous portion of the protein isolated from Gal-Gal pili. A more detailed description of the nature of Gal-Gal pili and the features that distinguish them from pili in general is set forth below.

"Antigenic determinant" refers to a domain within a peptide sequence which is capable of eliciting antibodies and capable of binding to them.

B. General Description of the Invention and Preferred Embodiments

B.1 The Nature of Pilus Protein and Its Relationship to Infection

An essential virulence factor associated with infection is the ability of the infecting bacterium to adhere to its target tissue. This adherence capability appears associated with pili which are proteinaceous surface filamentous structures of the bacterium. These filaments are aggregates of identical subunits (pilin) of moderate sequence length. The *E. coli* which are believed to be associated with uropathogenic infections have at least three types of chromosomally encoded pili: "Common" or "MS"; "Gal-Gal", and "X". They are classified by their binding specificity.

Common (or Type I or mannose binding or MS) pili agglutinate guinea pig erythrocytes and yeast cells and bind the Tamm-Horsfall uromucoid, which is a highly mannosylated glycoprotein secreted by the kidney of all placental mammals. Mannose containing saccharides, such as mannose itself, methyl mannoside, and yeast mannan, competitively inhibit binding. MS pili are found on 85% of all *E. coli* strains regardless of source.

Gal-Gal pili mediate hemagglutination of human erythrocytes in the presence of D-mannose and bind to voided uroepethelial cells. The majority of these strains produce pili that bind to two neutral structurally related glycosphingolipids, globotetraosyl ceramide and trihexosyl ceramide, which are normally present on human erythrocytes and uroepethelial cells. Such pili are found associated with approximately 30% of fecal *E. coli* strains, but are represented in 90–100% of strains isolated from cases of acute, non-obstructive pyelonephritis in children or from the urinary tracts of normal adult women subjects. It has been shown that the disaccharide α-Gal (1–4) β-Gal (Gal-Gal) is the active, minimal receptor recognized by these pili.

The X type pilus protein refers to the remaining proteins which do not fall into either of the two above groups; the nature of their receptors is unknown.

Many *E. coli* strains contain pili of all of the foregoing types. For example, *E. coli* strain J96, an isolate from a human pyelonephritis episode, contains two distinct chromosomal genes encoding pili. These sequences are obtained from restriction digests and isolated. One gene encodes MS pili and the other Gal-Gal pili. Using these fragments, transformed recombinant cells expressing only the gene for MS pili (SH48) and expressing only the gene for Gal-Gal pili (HU849) have been prepared by Hull, et al, *Infect Immun* (1981) 33:933. These strains were used as the source of pilus proteins in the examples below. Strains containing only MS pili were referenced to by Hull as MSHA+, and in particular one such strain was designated HU808. Strains containing only Gal-Gal pili were designated MRHA+; in particular, one such strain was designated HU807. The numbers HU808 and HU807 correspond to SH48 and HU849, respectively, as used herein. However using analogous techniques, other suitable recombinant strains may be prepared and used as pilin sources; non-recombinant wild type or mutant strains may also be used, if, indeed, they produce the desired pilin.

B.2 Features of the Gal-Gal-Pilus Protein and its Antigenic Determinants

As set forth in more detail below, the Gal-Gal pilus protein associated with a typical uropathogen was purified and sequenced. The results are shown in FIG. 1. Its N-terminal sequence is compared with the sequence of a similarly purified MS pilus protein as shown in FIG. 2. When cysteine residues are aligned, the first 46 positions are about 27% homologous. However, the antibodies elicited in rabbits after immunization with purified preparations of these proteins are only about 5% cross reactive.

The Gal-Gal associated pilin contains 163 amino acids and at least four regions of antigenic specificity: the sequence comprising residues 15–70 inclusive which can be isolated as a hydroxylamine II fragment, amino acids 133 to 163 isolated as a CNBrHFBA III fragment; the sequence corresponding to the tryptic IX fragment which comprises amino acids 79–110 and the sequence corresponding to the tryptic X fragment which is represented by the sequence of amino acids 111 to 125. These portions are underlined in FIG. 1.

The sequences representing the antigenic determinants can be isolated from the digest of purified protein, or can be prepared using recombinant or chemosynthetic techniques. The determinants referred to are intended to correspond approximately to the antigenic regions in question, but may contain additional or fewer amino acids so long as functionality is retained. These antigenic determinant regions are used to prepare vaccines, either as individual peptides, as combinations of peptides, as fragments of pili or as purified pilus protein. Antibodies formed in response to the vaccine serve as protection for the subject against subsequent infection by *E. coli* which cause urinary tract infections.

B.3 Preparation of the Polypeptide Active Ingredients

The desired polypeptides which serve as the active ingredients of the vaccines of the invention are most conveniently prepared, depending on their size, by one of three basic approaches.

If the desired sequence is short, e.g., that corresponding to the amino acid sequence constituting positions 111 to 125 of *E. coli* HU849 Gal-Gal pilin—a polypeptide having only 15 amino acids in the sequence—chemical synthesis, using methods now standard in the art, is feasible. A review of such methods is given by, for example, Margolin, A., et al, *Ann Rev Biochem* (1970) 39:841. In most of these procedures, the C-terminal amino acid is bound to a solid support, and reacted with the next amino acid in sequence which has been protected at the amino group to prevent self-condensation. After the initial coupling, the $NH_2$ protecting group is removed, and the coupling process repeated with the amino acid next in order. Polypeptides of considerable chain length have been synthesized in this way. The only requirement is that the amino acid sequence desired to be produced be known.

Since the polypeptides and protein of the invention are produced as part of a larger sequence in the pili or as the pilus protein of bacteria, they are available in quantity from fermenter cultures. They can be prepared by purification of the pilus protein, followed, if desired, by generation of the fragments by various hydrolysis techniques, and purification of the desired fragments. Conventional procedures are used in the purification of the pilus protein, in hydrolysis and in fragment purification.

Recombinant DNA methodology provides an alternative way of synthesizing the desired peptides or protein. The DNA coding sequence for the desired peptide or protein is ligated into an expression vector suitable for transforming a recipient strain, which is thus caused to express the gene and produce the protein. The DNA coding sequences, if sufficiently short, can be prepared synthetically using means known in the art. For longer sequences cDNA or a genomic digest can be used. Since the amino acid sequence is disclosed herein, appropriate single-stranded DNA probes can be constructed to probe a cDNA library prepared from mRNA of Gal-Gal pilus protein-producing strains. Alternatively, a genomic library can be created by restriction enzyme digests of the chromosome from Gal-Gal pilus protein-producing *E. coli* and probed in a manner similar to that used to probe the DNA, or the fragments can be directly inserted into expression vectors for transformation into a recipient strain, where successful transformants are screened for production of a protein which binds to Gal-Gal receptors. This was, indeed, the method used by Hull, et al, (supra), to prepare strain HU849.

Whether derived from a genomic or cDNA library, or by oligonucleotide synthesis using chemical methods, the coding sequence is placed under the control of promoter sequences compatible with bacterial hosts in plasmids containing convenient restriction sites for insertion of the desired coding sequence. Typical of such plasmids are, for example, pUC8, and pUC13 available from Messing, J., at the University of Minnesota; (see, e.g., Messing, et al, *Nucleic Acids Res* (1981) 9:309) or pBR322, available from New England Biolabs. Suitable promoters include, for example the -lactamase (penicillinase) and lactose (lac) promoter systems (Chang, et al, *Nature* (1977) 198:1056 and the tryptophan (trp) promoter system (Goeddel, D., et al, *Nucleic Acids Rec* (1980) 8:4057). The resulting expression vectors are transformed into suitable bacterial hosts using the calcium chloride method described by Cohen, S. N., et al, *Proc Natl Acad Sci* USA (1972) 69:2110. Successful transformants may produce the desired polypeptide fragments at higher levels than those found in recombinant or native strains normally producing Gal-Gal pili.

B.4 Vaccine Preparation

Preparation of vaccines which contain peptide sequences as active ingredients are well understood in the art. Typically, such vaccines are prepared as injectables, either as liquid solutions or suspensions; solid forms suitable for solution or suspension in liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of manitol, lactose, starch, magnesium sterate, sodium saccharrine, cellulose, magnesium carbonate and the like. These compositions take the form of solutions, suspensions, tablets, pills, capsules, sustained release formulations or powders and contain 10%-95% of active ingredient, preferably 25-70%.

As is understood in the art, the proteins of the present invention are present as neutral or salt forms depending on the pH of the surrounding medium, or of the medium from which they have been precipitated or crystallized. Accordingly, the amino acid sequences of the invention include their pharmaceutically acceptable salts, including the acid addition salts (formed with the free amino groups of the peptide) and which are formed with inorganic acids such as, for example, hydrochloric or phosphoric acids, or such inorganic acids as acetic, oxalic, tartaric, mandelic, and the like. Salts formed with the free carboxYl groups may also be derived from organic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges for subcutaneous or muscular injection are of the order of 50–500 $\mu$g active ingredient per individual. For oral, rectal suppository, urethral or vaginal preparation, large amounts of about 100 $\mu$g-1 mg would be used. Suitable regimes for initial administration and booster shots are also variable, but are typified by an initial administration followed in one-two week intervals by a subsequent injection or other administration.

C. Examples

The following serve to illustrate but not to limit the invention. Paragraph C.1 sets forth the basis for the association of Gal-Gal pilus protein with urinary tract infections; Paragraph C.2 describes preparation of the active ingredient(s); Paragraph C.3 describes the use of purified Gal-Gal protein and of peptides comprising specific antigenic determinants to elicit antibodies and to protect the host organism.

C.1 Correlation of Gal-Gal Pilus Protein with Urinary Tract Infection Cultures Urinary tract infections in general can be exemplified by pyelonephritis. In the course of this disease, the bacteria enter the urinary tract, adhere to and colonize the mucosa, and ultimately infect the host.

Two approaches established the role of Gal-Gal pili in mediating colonization of the urinary tract: (1) intravesicular administration of strains containing a variety of pili types, followed by assay for their presence in the host, and 2) determination of the distribution of pilus receptor carbohydrates in the urinary tract, coupled with assay for inhibitors of binding.

C.1.a Intravesicular Administration

Sixteen-week-old Balb-c female mice were used. These mice were initially raised in a pathogen-free environment and were administered a non-pathogenic defined bacterial gastrointestinal flora. Previous experience with such mice has shown that the kidneys are sterile and that there are no gram-negative bacteria colonizing the urine.

Innocula containing varying numbers of colony-forming units (CFU) from *E. coli* strains J96, HU849, SH48, or HB101 (a non-piliated *E. coli* K12 derivative which was used as the recipient of the recombinant vectors) were administered into the bladder via catheter and the catheter then removed. In initial experiments, $10^6$ CFU ($10^5$ CFU for J96) formulated to 100 $\mu$l derived from bacteria which had been grown overnight in trypticase soy broth (TSB) for 18 hours at 37° C. were used. In subsequent experiments, increasing levels of CFU were administered; for CFU $10^8$ or more, a 250 $\mu$l volume was used, resulting in acute ureteric reflux.

Two days later the mice were killed by prolonged ether anesthesia, and both urine and kidney tissues were assayed for the presence of bacterial growth. To assay urine, the bladder area was massaged to express urine, and a sterile 10 $\mu$l loop used to inoculate 0.5 cm² trypticase soy agar (TSA) or TSA supplemented with antibiotics. The plates were incubated for 18-24 hours at 37° C. and read by grading the visible growth. The identity of the growth observed with the administered strain was verified as follows: cultures were positive for *E. coli*

J96 if the organisms grown on TSA plates were predominantly gram-negative and agglutinated by rabbit anti-J96 O sera (1:1000 dilution in PBS) in a slide agglutination assay. Cultures were confirmed as positive for SH48 if organisms on TSA supplemented with chloramphenicol (25 µg/ml) were predominantly gram-negative, capable of agglutinating Syn Man-Man absorbed to latex beads (Chem Biomed) in a slide agglutination assay and agglutinated by rabbit anti-SH48 pilus sera (1:1000 dilution in PBS). Cultures were confirmed as positive for HU849 if organisms on TSA supplemented with tetracycline (20 µg/ml) were predominantly gram-negative, capable of Gal-Gal agglutination, and agglutinated by rabbit anti-HU849 pilus sera (1:1000 dilution in PBS). Cultures were confirmed positive for HB101 if organisms on TSA were predominantly gram-negative, incapable of Syn Man-Man or Gal-Gal agglutination, and not agglutinated by anti-pilus sera.

Kidneys were excised by sterile techniques and sagitally sectioned through the mid-pelvis, and a cut surface was streaked onto a TSA or antibiotic supplemented TSA. The remainder of the assay was as described for urine samples in the previous paragraph.

The results are shown in the table below as the ratio of the number of animals giving positive evidence of the presence of the strain used as inoculum in the indicated tissue to the number of animals examined.

| BALB/c Mouse Model of *E. coli* Pyelonephritis | | | | | |
|---|---|---|---|---|---|
| | | | Colonization | | Renal |
| Strain | Pilus Type | Inoculum | Urine | R-Kidney | Invasion |
| J96 | MS and | $10^5$ | 4/7 | 5/7 | N.D. |
| | Gal-Gal | $10^6$ | 8/8 | 9/9 | 9/9 |
| | | $10^8$ | 5/5 | 5/5 | 5/5 |
| SH48 | MS | $10^6$ | 4/8 | 0/8 | 0/8 |
| | | $10^8$ | N.D. | 0/7 | N.D. |
| | | $10^{10}$ | N.D. | 5/7 | N.D. |
| | | $10^{12}$ | N.D. | 6/6 | 0/3 |
| HU849 | Gal-Gal | $10^6$ | 8/9 | 10/10 | 0/10 |
| HB101 | None | $10^6$ | 0/11 | 0/5 | 0/5 |
| | | $10^{12}$ | 0/5 | 0/5 | N.D. |

The results show that only strains containing Gal-Gal pili were effective in colonizing the kidney at any reasonable level of inocculum.

Renal invasion as shown in the last column of the table was assessed by light microscopy of sections stained by hematoxylin/eosin or Giemsa stains. Also, immunoperoxidase histological assay was used to confirm renal invasion in mice administered J96, (Sternberger, L. *Immunocytochem* (1979) 2nd Wiley & Sons, New York). Although the HU849 strain (containing Gal-Gal pilus) was effective in colonizing the kidney, it was not capable of renal invasion. Indeed, renal invasion was successful only with the wild type strain (J96). This would be expected, of course, as the recombinant strains represent non-virulent *E. coli* transformed with coding sequences for the designated pilus proteins. Other virulence factors would be presumed to be missing from the strain.

C.1.b Distribution of Tissue Pilus Receptor Carbohydrates and of Soluble Pilus Binding Factors The urinary tracts of the BALB/c mice were assessed for receptors for MS and Gal-Gal pili and for soluble urine factors which are capable of binding to these. To assess for the presence of pili on the receptors, immunohistochemical staining using an avidin-biotin-peroxidase complex assay was used. It employed formalin fixed paraffin sections.

The sections were dewaxed through xylol, cleared with graded alcohols, and mounted on glass slides. The slides were flooded with normal goat serum (DAKO Accurate Chemical Corp., Hicksville, N.Y.) diluted 1:10 in PBS with 1% (w/v) BSA(PBSA) for 30 min to reduce nonspecific binding of antisera. Excess serum was removed by blotting and the sections then incubated for 1 hour at room temperature with either rabbit anti-Syn Gal-Gal or anti-Syn Man-Man (diluted 1:50 in PBSA). The slides were washed in PBS and the sections then incubated for 30 min at room temperature with biotinylated goat anti-rabbit antibody (Vector Laboratories, Burlingame, CA). After the slides were repeatedly washed in PBS, the Vectastain TM ABC reagent was applied for 60 min at room temperature and then removed by washing in PBS. These sections were developed for 5 min at room temperature in 0.01% (v/v) hydrogen peroxide and 0.05% (w/v) diaminobenzidene tetrahydrochloride (Sigma) in 0.05M Tris buffer, pH 7.2. The slides were thoroughly washed in distilled water, hematoxylin counterstained and mounted. Sections were examined under the light microscope and the brown color reaction product graded. The negative control was normal rabbit serum substituted for the primary antisera. The antibody specificity was confirmed by (1) absorption of primary antisera with the homologous (10% w/v) hapten and (2) substitution of the biotinylated antibody and the ABC Reagent with PBSA.

Distribution of the receptors was evaluated in bladder, ureter and kidney tissues. Epithelial and related cell types in the urinary tract showed a high density of receptors corresponding to both MS and Gal-Gal pili. The distribution for both types of pili was similar.

Determination of a possible urine soluble pilus receptor was made by assessing inhibition of pilus binding to its specific carbohydrate receptor using an ELISA inhibition assay. The presence of such a soluble factor was confirmed for MS pili, but absent for Gal-Gal pili.

These results are consistent with the view that urinary tract colonization by *E. coli* is mediated by Gal-Gal pili, not because MS receptors are absent, but because their capacity to mediate adherence to the uroephithelium is inhibited by uromucoids, presumably the highly mannosylated Tamm-Horsfall protein.

The ability of Gal-Gal pilus protein to protect against urinary tract infection was assessed as set forth below: Pilus protein was purified, formulated into a vaccine and the vaccine used to innoculate groups of BALB/C mice. Sera were analyzed for antibody formation, and response ascertained to subsequent challenge with the wild type infectious agent, *E. coli* J96.

C.2 Purification of Pilus Protein

Pili from strains SH48 and HU849 were purified from organisms grown on TSA for 18 hours at 37° C., basically according to the method of Brinton, C. *Trans N Y Acad Sci* (1965) 27:1003. Briefly, the cells were harvested into ice-cold 0.005 M Tris buffer, pH 8.3 (T-buffer). Pili were sheared from the bacterial surface in a Sorval Omnimixer (4000 rpm for 30 minutes at 4° C.) and depiliated organisms and debris were removed by centrifugation. The pili were precipitated in 0.5 M Tris buffer and 0.15 M NaCl, pH 7.0, by the addition of $MgCl_2$ to 0.1 M (TSM buffer). The aggregated pilus fragments were then collected by centrifugation, the pellet was dissolved in T-buffer and insoluble impurities removed by centrifugation.

The pili were re-precipitated in TSM buffer and separated from soluble impurities by centrifugation. After 6 cycles of precipitation and solubilization in TSM and T-buffer respectively, the pilin preparations were extensively dialyzed against double-distilled deionized water.

The purity of the resulting proteins was confirmed by electron microscopy, SDS-PAGE, amino terminal sequence analysis, and by assessment of the level of lipopolysaccharide (LPS) contamination.

For electron microscopy samples were negatively stained with 2% (w/v) aqueous uranyl acetate on copper grids coated with Formvar and carbon.

SDS-PAGE was performed according to the method of Laemmli *Nature* (1970) 227:680. Because MS pili do not enter the stacking gel under these conditions, SH48 pili were depolymerized before electrophoresis by the addition of KCl, pH 1.8, according to the method of McMichael, J. C., et al, *J.Bacteriol* (1979) 138:969. Gels were stained with Coomassie brilliant blue R250 (Sigma Chemical Co., St. Louis, MO) or silver (Morrissey, J., *Anal Biochem* (1982) 117:307) for protein detection; and also oxidized with periodic acid and then silver stained (Tsai, G.M., et al, *Anal Biochem* (1982) 119:115) for the detection of contaiminating LPS.

LPS was also estimated by determining the 2-keto-3-deoxyoctanoate content of 500 to 1000 ug samples using the method of Waravdekar, V., et al, *J Biol Chem* (1959) 234:1945 by relating their optical density at 548 nm to standard curves derived from LPS prepared from *E. coli* strains HB101 and J96 by the phenol-extraction method of Westphal, 0., et al, *Meth Carbohyd.Chem* (1965) 5:80.

N-terminal sequencing was performed by automated Edman degradation with a Beckman 890C liquid-phase sequencer (Beckman Instruments, Palo Alto, CA) using a 0.1 M Quadrol program. Each amino acid phenylthiohydantoin (PTH) derivative was identified and quantitated by reverse-phase high pressure liquid chromatography and confirmed by gas-liquid chromatography and/or thin-layer chromatography. The complete sequence of the Gal-Gal pilin derived from HU849 was determined using multiple hydrolyzates containing overlapping fragments whose sequences were determined as set forth above.

The purified pilus protein preparations were found to be free of both RNA and DNA and to be 97-99% homogeneous according to SDS-PAGE. These preparations were confirmed by electron microscopy to be composed of homologous filaments with minimal non-filamentous structures. The LPS content was less than 0.1% as measured by the 2-keto-3-deoxyoctanoate (KDO) assay and less than 0.01% as assessed by lack of silver stain corresponding to LPS on gels.

The N-terminal amino acid sequences were determined unambiguously to be as set forth in FIG. 2; the complete amino acid sequence of the HU849 pilin is set forth in FIG. 1.

C.3 Immunization

The test vaccines employed the purified pilus protein prepared as described above, and control vaccines were prepared from somatic O-antigens from HB101 and J96. A buffer control was also used.

Pilus vaccines from SH48 or HU849 were prepared using 50 μg of protein in 1 ml PBS, pH 7.4, emulsified with 1 ml of complete Freund's adjuvant. The resulting 2 ml of vaccine was administered in multiple subcutaneous and intramuscular injections. Somatic 0 antigen innocula from J96 and HB101 strains were prepared by suspending $10^8$ heat-killed bacteria in 1 ml PBS, and emulsifying the resultant in an equal volume of adjuvant.

C.3.a Resistance to Challenge

The animals were challenged after two weeks by administration of $10^6$ CFU *E. coli* J96 in 100 μl by intraurethral catheterization as described in Paragraph C.1. Two days later, the mice were exsanguinated, and sera obtained for antibody titer and kidneys were excised and sagitally sectioned through the mid-portion to assess specifically for J96 colonization as described above. To assay for invasion, renal pelvic sections were also processed for standard light microscopy by staining with hematoxylin/eosin, and Giemsa stains, and by immunoperoxidase staining, as described above.

The results shown in the table below, indicate the ratio of the number of animals showing positive J96 colonization or invasion to the number of mice.

| | Vaccination Trial with a Variety of Immunogens in the Prevention of *E. coli* Pyelonephritis | | | |
|---|---|---|---|---|
| | J96 Colonization | | | J96 Renal Invasion |
| Immunogen | +Urine # mice | +R Kidney # mice | +L Kidney # mice | + Invasion # mice |
| Buffer Control | 8/8 | 8/8 | 8/8 | 4/4 |
| Somatic 0 HB101 | 4/4 | 4/4 | 4/4 | 4/4 |
| Somatic 0 J96 | 4/4 | 4/4 | 4/4 | 4/4 |
| SH48 Pili (MS-pili) | 8/8 | 8/8 | 8/8 | 4/4 |
| HU849 pili (Gal-Gal pili) | 3/22 | 2/22 | 2/22 | 1/11 |

Thus, attempts to protect mice from challenges against J96 infection vaccination using protein other than Gal-Gal pili failed uniformly by every criterion tested. Only the Gal-Gal pili vaccine recipients were protected from J96 colonization and renal invasion.

C.3.b. Immunogenicity

The presence of antibodies to Gal-Gal pilus protein in the sera of mice immunized with the pili preparation from HU849 was confirmed by a direct ELISA assay for IgG antibody specific to Gal-Gal pili. This procedure is described by Normark, S., et al, *Infect Immun* (1983) 41:942. Anti Gal-Gal titers of ≧1:10,000 were obtained in mice administered the pili, and correlatd with protection. In two mice which were colonized by J96, the titers were only 1:100.

C.4 Alternate Vaccines Using Antigenic Determinants

Overlapping fragments of the HU894 protein purified as discribed in Paragraph C.2 were obtained by enzymatic and chemical digestion using, for example, carboxypeptidases, partial acid hydrolysis, trypsin digestion of pili modified by citroconylation/acetylation, and cyanogen bromide-HFBA. Purification and analysis of the resulting fragments also utilized conventional methods, such as affinity, reverse phase, and ion exchange chromatography, gel filtration and electrophoresis.

In a typical purification of the individual fragments the digest was applied to a C-18 reverse phase HPLC column and eluted in 0.1% trifluoroacetic acid buffer using a 0-80% acetonitrile linear gradient. Protein containing fractions were further purified using high voltage paper electrophoresis in pyridine/acetate buffer, pH 6.4.

The fragments obtained using the foregoing methods were assessed for their ability to behave as antigenic determinants, based on either Western Blot or ELISA assays, employing rabbit antisera raised against Gal-Gal pili.

The ELISA assay was essentially that described by Normark, et al (supra). Briefly, disposable microtiter plates (Cooke Polystyrene, 96 U wells) were used. The wells were sensitized with 100 μl of a 1 μg/ml solution of the fragment to be tested in 0.1 M sodium carbonate buffer, pH 9.6, for 12 hours at room temperature, and the wells then washed 3 times in NaCl/Brij. 100 μl of rabbit anti-Gal-Gal serum diluted 1:10,000 was incubated in the wells for 3 hours at 37° C. The wells were then washed 3 times with NaCl/Brij, and 100 μl alkaline phosphatase conjugated goat anti-rabbit IgG (Miles Laboratories, Bethesda, Maryland) diluted 1:1000 in NaCl/Brij was added to each well and incubated 1 hour at 37° C. The plates were again washed with NaCl/Brij and 1 mg/ml of p-nitrophenyl phosphate (Sigma) in 0.1 M diethanolamine buffer, pH 9.8, was added to each well; and the plates incubated 10 minutes at 37° C. The reaction was stopped by the addition of 10 μl 2 N NaOH per well and the absorbance determined at 405 nm with an MR 580 Micro-ELISA Autoreader (Dynatek).

Western Blots were performed as described by Towbin, H., et al, *Proc Natl Acad Sci* (USA) (1979) 76:4350 or Swanson, J., et al, *Infect Immun* (1982) 38:668.

Four fragments were found which gave positive results in these assays: the amino acid sequence containing the residues at positions 15 and 70 inclusive, which results from digestion by hydroxylamine; the amino acid sequence between positions 133 and 163 inclusive, which results from CNBr/HFBA digestion; and 2 fragments resulting from trypsin digestion, the amino acid sequence between positions 79–110 inclusive (trypsin fragment IX) and that between positions 111 and 125 inclusive (trypsin fragment X). The sequences of these fragments are underlined in FIG. 1.

Accordingly, following the procedures set forth in Paragraph C.3, but substituting for the Gal-Gal purified pilus protein any of the foregoing fragments, vaccines effective against uropathogens are prepared and administered.

In summary, it has been shown that urinary tract infections are mediated specifically by the Gal-Gal pili associated with *E. coli* causing this infection. A pilus vaccine is effective in protecting subject mammals against challenge by wild type infectious bacteria known to cause human urinary tract infections. Certain portions of this 163 amino acid protein have been shown to be responsible for the antigenic activity of this protein, thus, vaccines composed of these fragments or of purified pilin are suitable for use in immunizing populations at risk against urinary tract infections.

We claim:

1. A composition of matter which consists essentially of the peptide:

Ala Pro Thr Ile Pro Gln Gly Gln Gly Lys Val Thr
Phe Asn Gly Thr Val Val Asp Ala Pro Cys Ser Ile
Ser Gln Lys Ser Ala Asp Gln Ser Ile Asp Phe Gly
Gln Leu Ser Lys Ser Phe Leu Glu Ala Gly Gly
Val Ser Lys Pro Met Asp Leu Asp Ile Glu Leu Val
Asn Cys Asp Ile Thr Ala Phe Lys Gly Gly Asn
Gly Ala Lys Lys Gly Thr Val Lys Leu Ala Phe
Thr Gly Pro Ile Val Asn Gly His Ser Asp Glu Leu
Asp Thr Asn Gly Gly Thr Gly Thr Ala Ile Val Val
Gin Gly Ala Gly Lye Asn Val Val Phe Asp Gly
Ser Glu Gly Asp Ala Asn Thr Leu Lys Asp Gly
Glu Asn Val Leu His Tyr Thr Ala Val Val Lys
Lys Ser Ser Ala Val Gly Ala Ala Val Thr Glu Gly
Ala Pha Ser Ala Val Ala Asn Phe Asn Leu Thr
Tyr Gln.

2. A composition of matter consisting essentially of a peptide selected from the group consisting of Gly Thr Val Val Asp Ala Pro Cys Ser Ile Ser Gln
Lys Ser Ala Asp Gln Ser Ile Asp Phe Gly Gln Leu
Ser Lys Ser Phe Leu Glu Ala Gly Gly Val Ser Lys
Pro Met Asp Leu Asp Ile Glu Leu Val Asn Cys
Aap Ile Thr Ala Phe Lys Gly Gly Asn;

Leu Ala Phe Thr Gly Pro Ile Val Asn Gly His Ser
Asp Glu Leu Asp Thr Asn Gly Gly Thr Gly Thr
Ala Ile Val Val Gln Gly Ala Gly Lys;

Asn Val Val Phe Asp Gly Ser Glu Gly Asp Ala Asn
Thr Leu Lys; and

Tyr Thr Ala Val Val Lys Lys Ser Ser Ala Val Gly
Ala Ala Val Thr Glu Gly Ala Phe Ser Ala Val Ala
Asn Phe Asn Leu Thr Tyr Gln.

3. A vaccine effective in protecting mammals against urinary tract infections, which vaccine comprises an immunogenic form of a peptide consisting essentially of the amino acid sequence:

Ala Pro Thr Ile Pro Gln Gly Gln Gly Lys Val Thr
Phe Asn Gly Thr Val Val Asp Ala Pro Cys Ser Ile
Ser Gln Lys Ser Ala Asp Gln Ser Ile Asp Phe Gly
Gln Leu Ser Lys Ser Phe Leu Glu Ala Gly Gly
Val Ser Lys Pro Met Asp Leu Asp Ile Glu Leu Val
Asn Cys Asp Ile Thr Ala Phe Lys Gly Gly Asn
Gly Ala Lys lys Gly Thr Val Lys Leu Ala Phe Thr
Gly Pro Ile Val Asn Gly Gis Ser Asp Glu Leu Asp
Thr Asn Gly Gly Thr Gly Thr Ala Ile Val Val Gln
Gly Ala Gly Lys Asn Val Val Phe Asp Gly Ser
Glu Gly Asp Ala Asn Thr Leu Lys Asp Gly Glu
Asn Val Leu His Tyr Thr Ala Val Val Lys Lys Ser
Ser Ala Val Gly Ala Ala Val Thr Glu Gly Ala Phe
Ser Ala Val Ala Asn Phe Asn Leu Thr Tyr Gln.

4. A vaccine effective in protecting mammals against urinary tract infections which vaccine comprises an immunoprotectively effective amount of an immunogenic form of a peptide consisting essentially of an amino acid sequence selected from the group consisting of Gly Thr Val Asp Ala Pro Cys Ser Ile Ser Gln Lys
Ser Ala Asp Gln Ser Ile Asp Phe Gly Gln Leu Ser
Lys Ser Phe Leu Glu Ala Gly Gly Val Ser Lys Pro
Met Asp Leu Asp Ile Glu Leu Val Asn Cys Asp Ile
Tyr Ala Phe Lys Gly Gly Asn;

Leu Ala Pha Thr Gly Pro Ile Val Asn Gly His Ser
Asp Glu Leu Asp Thr Asn Gly Gly Thr Gly Thr
Ala Ile Val Val Gln Gly Ala Gly Lys;

Asn Val Val Phe Asp Gly Ser Glu Gly Asp Ala Asn
Thr Leu Lys; and

Tyr Thr Ala Val Val Lys Lys Ser Ser Ala Val Gly
Ala Ala Val Thr Glu Gly Ala Phe Ser Ala Val Ala Asn
Phe Asn Leu Thr Tyr Gln said peptide conjugated to a carrier if needed to render it in an immunogenic form.

5. A vaccine effective in protecting mammals against urinary tract infections, which vaccine comprises an immunoprotectively effective amount of an imnunoganic form of a peptide consisting essentially of a sequence of at least 15 amino acids corresponding to at least one antigenic determinant of *E. coli* Gal-Gal pilus protein, in combination with a pharmaceutically acceptable carrier.

6. A method of protecting a subject mammal against urinary tract infection which method comprises administering to a subject in need of such protection an effective amount of the vaccine of claim 5.

7. The vaccine of claim 5 which comprises a peptide having the complete amino acid sequence of an *E. coli* Gal-Gal pilus protein.

* * * * *